United States Patent [19]
Bernasconi

[11] 3,974,280
[45] Aug. 10, 1976

[54] BENZOTHIOPHENES
[75] Inventor: Raymond Bernasconi, Oberwil, Switzerland
[73] Assignee: Ciba-Geigy Corporation, Ardsley, N.Y.
[22] Filed: Dec. 3, 1974
[21] Appl. No.: 529,174

[30] Foreign Application Priority Data
Dec. 6, 1973 Switzerland.................. 17107/73
Aug. 30, 1974 Switzerland.................. 11838/74

[52] U.S. Cl............................ 424/263; 260/293.57; 260/294.8 C; 424/267
[51] Int. Cl.²......................................... A61K 9/22
[58] Field of Search............... 260/293.57, 294.8 C; 424/263, 267

[56] References Cited
UNITED STATES PATENTS
3,070,606 12/1962 Anderson...................... 260/330.5
3,855,242 12/1974 Chapman et al............... 260/330.5

*Primary Examiner*—G. Thomas Todd
*Attorney, Agent, or Firm*—Joseph G. Kolodny; John J. Maitner; Theodore O. Groeger

[57] ABSTRACT

The invention relates to a process for the production of new benzo[b]thiophenes of formula I

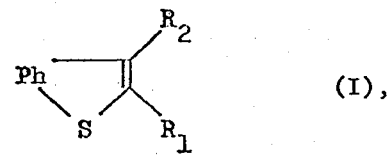

wherein
pH is optionally substituted o-phenylene, one of the radicals $R_1$ and $R_2$ is hydrogen or lower alkyl, and the other of the radicals $R_1$ and $R_2$ is optionally C-substituted piperidyl which optionally carries hydroxy on the ring-C-atom bound to the benzo[b]thienyl radical, or which optionally contains a C-C-double bond emanating from this C-atom, and which optionally carries on the N-atom a hydrocarbon radical of aliphatic character, which radical is optionally substituted in a position higher than the 1-position, and of their acid addition salts.

These new compounds possess valuable pharmacological properties. In particular they inhibit mono-amine oxidase and further inhibit the absorption of noradrenaline and serotonine in the brain. They are useful as active substances for pharmaceutical preparations for the treatment of mental depressions and psychoses.

21 Claims, No Drawings

BENZOTHIOPHENES

DETAILED DESCRIPTION

The invention relates to benzo[b]thiophenes of formula I

wherein

Ph is optionally substituted o-phenylene, one of the radicals $R_1$ and $R_2$ is hydrogen or lower alkyl, and the other of the radicals $R_1$ and $R_2$ is optionally C-substituted piperidyl which optionally carries hydroxy on the ring-C-atom bound to the benzo[b]thienyl radical, or which optionally contains a C-C-double bond emanating from this C-atom, and which optionally carries on the N-atom a hydrocarbon radical of aliphatic character, which radical is optionally substituted in a position higher than the 1-position, and to their acid addition salts, to processes for the production of these compounds, as well as to pharmaceutical preparations containing these compounds.

By a lower radical is meant, in the foregoing and in the following, a radical having preferably up to 7 C-atoms, especially one having up to 4 C-atoms.

A radical of aliphatic character is a radical of which the free valency proceeds from a C-atom which is not a member of an aromatic system.

Optionally substituted o-phenylene is, for example, o-phenylene which optionally carries one or more, preferably up to three, more particularly two or one, substituent(s) such as nitro, trifluoromethyl, loweralkylidenedioxy, arylmethoxy, cycloalkyl, 1-hydroxycycloalkyl, 1-cycloalken-1-yl and, in particular, lower alkyl, lower alkoxy, halogen, hydroxy or, corresponding to a fused-on benzene ring, 1,4-butadienylene, which is bound, in particular, in the positions 4 and 5, or 5 and 6, of the benzo[b]thienyl radical, or trimethylene or tetramethylene which is bound, in particular, in the positions 5 and 6. Ph is especially unsubstituted o-phenylene.

Lower-alkylidenedioxy is, for example, ethylidenedioxy and, in particular, methylenedioxy.

Arylmethoxy is, in particular, benzyloxy optionally substituted in the phenyl moiety, with substituents to be mentioned being: lower alkyl, lower alkoxy, halogen and/or trifluoromethyl. Optionally substituted benzyloxy contains one or more, especially up to two, but preferably one, substituent(s); it is primarily, however, unsubstituted benzyloxy.

Cycloalkyl is, for example, that having 3–10 C-atoms, especially that having 3–8 ring-C-atoms, such as optionally lower-alkylated, preferably however unsubstituted, cyclopropyl, cyclobutyl, cycloheptyl, cyclooctyl and, in particular, cyclopentyl and cyclohexyl. 1-Hydroxycycloalkyl and 1-cycloalken-1-yl contain, for example, 5–10 C-atoms, of which 5–8 are ring-C-atoms, such as optionally lower-alkylated, preferably however unsubstituted, 1-hydroxycycloheptyl, 1-hydroxycyclooctyl or 1-cyclohepten-1-yl or 1-cycloocten-1-yl and, in particular, 1-hydroxycyclopentyl, 1-hydroxycyclohexyl or 1-cyclopenten-1yl or 1-cyclohexen-1-yl.

Lower alkyl is, for example, ethyl, n-propyl, isopropyl, straight-chain or branched-chain butyl, pentyl, hexyl or heptyl, and expecially methyl, all bound in any position.

Lower alkoxy is, for example, ethoxy, n-propoxy, isopropoxy, as well as butoxy, pentyloxy, hexyloxy or heptyloxy, wherein the alkyl moieties are straight-chain or branched-chain and are bound in any position, and particularly methoxy.

Halogen is, in particular, fluorine or bromine, and more particularly chlorine.

Optionally substituted piperidyl $R_1$ or $R_2$, which optionally carries hydroxy on the C-atom bound to the benzo[b]thienyl radical, or which optionally contains a C-C-double bond emanating from the C-atom bound to the benzo[b]thienyl radical, and which optionally carries on the N-atom a hydrocarbon radical of aliphatic character, which radical is optionally substituted in a position higher than the 1-position, is 2-, 3- or, in particular, 4-piperidyl having the above closer defined meaning.

The optionally substituted piperidyl $R_1$ or $R_2$ having the above closer defined definition is preferably that of the partial formula $I_o$

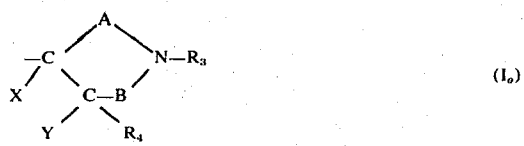

wherein

A and B represent bivalent, saturated aliphatic hydrocarbon radicals and one of these symbols can also represent the direct bond, with A and B together always having 3 chain members and containing together with $R_4$ at most 10 carbon atoms, $R_3$ represents a hydrocarbon radical of aliphatic character which is optionally substituted in a position higher than the 1-position, $R_4$ represents hydrogen or lower alkyl, and X and Y each represent hydrogen, or together they represent an additional bond.

As hydrocarbon radical of aliphatic character, which is optionally substituted in a position higher than the 1-position, the substituent on the N-atom of the piperidyl $R_1$ or $R_2$, just as the radical $R_3$ of the above partial formula, is, in particular, an aliphatic, cycloaliphatic, cycloaliphatic-aliphatic or araliphatic hydrocarbon radical optionally substituted in a position higher than the 1-position. Suitable substituents are, in particular, hydroxy, oxo or lower alkoxy.

Such an aliphatic hydrocarbon radical is, for example, lower alkyl, especially as given above, lower alkenyl such as 2-butenyl, 2-methallyl or, in particular, allyl, or lower alkynyl such as 2-propynyl. The aliphatic hydrocarbon radicals can be substituted by several, or especially by one, hydroxy group(s), oxo group(s) or lower alkoxy group(s), such as hydroxy-lower-alkyl, e.g., 2-hydroxyethyl, 2-hydroxy-n-propyl, 3-hydroxy-n-propyl, 3-hydroxy-n-butyl, or such as dihydroxy-loweralkyl, e.g., 2,3-dihydroxy-n-propyl, such as oxo-loweralkyl, e.g., acetonyl or 3-oxo-n-butyl, or such as loweralkoxy-loweralkyl, e.g., 2-methoxyethyl, 2-ethoxyethyl, 2-isopropoxy-ethyl, 3-methoxy-n-propyl or 2-n-butoxyethyl, or such as di-lower-alkoxy-lower-alkyl, e.g. 3,3-diethoxy-n-butyl or 2,3-dimethoxy-n-propyl.

Such a cycloaliphatic hydrocarbon radical is, e.g., a cycloalkyl radical having especially 3–10, particularly 3–6, ring members, such as cyclopropyl, cyclobutyl, cyclopentyl, cyclohexyl or cycloheptyl. The cycloaliphatic hydrocarbon radicals can be substituted by several, or particularly by one, hydroxy group(s), oxo group(s) or lower alkoxy group(s), such as 2-hydroxycyclohexyl or 2-oxo-cyclohexyl.

Such a cycloaliphatic-aliphatic hydrocarbon radical is, e.g., a cycloalkyl-lower-alkyl radical, especially a cycloalkyl-methyl radical or 2-cycloalkyl-ethyl radical, with the cycloalkyl moiety having particularly 3–10, more especially 3–6, ring members, such as cyclopropylmethyl, cyclobutylmethyl, 2-cyclopentyl-ethyl, cyclohexylmethyl, 2-norbornanylmethyl, bicyclo[2.2.-2]oct-2-ylmethyl or 1-adamantylmethyl.

Such an araliphatic hydrocarbon radical is, e.g., aryl-lower-alkyl or aryl-lower-alkenyl.

Aryl-lower-alkyl is, in particular, phenyl-lower-alkyl optionally substituted in the phenyl moiety. Aryl-lower-alkenyl is, in particular, phenyl-lower-alkenyl optionally substituted in the phenyl moiety. Suitable substituents are in both cases, in particular, lower alkyl, such as the above lower alkoxy, as mentioned above, and halogen as mentioned above. Furthermore, also the lower alkyl moiety can be substituted in a position higher than the 1-position, especially by lower alkoxy, as the above, and particularly by hydroxy or oxo. There can be several substituents present, preferably up to two, and in the case of the methoxy groups up to three; the unsubstituted radicals are however preferred, with there being present in the lower alkyl moiety, in particular, 1–3 C-atoms, and in the lower-alkenyl moiety preferably 2–4, especially 3, C-atoms, such as benzyl, chlorobenzyl, dichlorobenzyl, bromobenzyl, methylbenzyl, isopropylbenzyl, methoxybenzyl, dimethoxybenzyl, trimethoxybenzyl, ethoxybenzyl, isopropoxybenzyl, phenethyl, α-methylphenethyl, 3-phenylpropyl, β-hydroxyphenethyl, phenacyl and cinnamyl.

The compounds of formula I and their addition salts with inorganic and organic acids possess valuable pharmacological properties. After oral administration in the dosage range of from 30 to 100 mg/kg, they inhibit in the rat mono-amino oxidase, as is shown from the determination of the mono-amino oxidase activity in the total brain homogenate with serotonin as well as with phenylethylamine as substrate. Particularly pronounced is the inhibitory effect on the mono-amino oxidase in the case of such compounds of the general formula I wherein $R_1$ is piperidyl as given above, $R_2$ is hydrogen or lower alkyl, and Ph has the above meanings, and the addition salts thereof. At the same time, the compounds of the general formula I and their acid addition salts inhibit the absorption of noradrenaline and serotonin, as was established on the brain of the rat after oral administration of from 30 to 100 mg/kg. In addition, they potentiate, with oral administration to the mouse of doses of from 30 to 100 mg/kg, the action of 5-hydroxytryptamine. Together with a favourable therapeutic index, the above-mentioned properties characterise the compounds of the general formula I and their pharmaceutically acceptable acid addition salts as antidepressants which, for example, can be administered orally or parenterally for the treatment of metal depression.

Furthermore, compounds I wherein $R_1$ is hydrogen or lower alkyl, $R_2$ is piperidyl as given above, and Ph has the above meanings, and their pharmaceutically acceptable acid addition salts have a pronounced antipsychotic action, so that they can be advantageously used as antipsychotic agents.

Compounds of formula I that are of particular importance are those wherein Ph is o-phenylene unsubstituted or substituted by nitro, trifluoromethyl, loweralkylidenedioxy, arylmethoxy, lower alkyl, lower alkoxy, halogen, hydroxy, 1-hydroxycycloalkyl, 1-cycloalkenl-yl, cycloalkyl, 1,3-butadienylene, trimethylene or tetramethylene, $R_1$ or $R_2$ is piperidyl which at the ring-C-atom bound to the benzo[b]thienyl radical is unsubstituted or substituted by hydroxy or optionally contains a double bond emanating from this C-atom, and which at its other ring-C-atoms is unsubstituted or substituted by lower alkyl and which at its N-atom is unsubstituted or substituted by a hydrocarbon radical which is unsubstituted or substituted in a position higher than the 1-position, and $R_2$ or $R_1$ is hydrogen or lower alkyl.

To be particularly emphasised are compounds I, wherein Ph is o-phenylene unsubstituted or substituted by lower alkyl, lower alkoxy, halogen or hydroxy, $R_1$ or $R_2$ is piperidyl which at the ring-C-atom bound to the benzo[b]thienyl radical is unsubstituted or substituted by hydroxy or optionally contains a double bond emanating from this C-atom, and which at its other ring-C-atoms is unsubstituted or substituted by lower alkyl and which at its N-atom is unsubstituted or substituted by an aliphatic, cycloaliphatic, cycloaliphatic-aliphatic or araliphatic hydrocarbon radical, which is unsubstituted or substituted in a position higher than the 1-position, and $R_2$ or $R_1$ is hydrogen or lower alkyl.

Compounds I to be especially emphasized are those wherein Ph is o-phenylene unsubstituted or at most di-substituted by lower alkyl, lower alkoxy, halogen or hydroxy, $R_1$ or $R_2$ is piperidyl which optionally contains a C-C-double bond emanating from the ring-C-atom bound to the benzo[b]thienyl radical, and which at its other ring-C-atoms is unsubstituted or substituted by one lower alkyl, and which at its N-atom is unsubstituted or substituted by lower alkyl, lower alkenyl, lower alkynyl, cycloalkyl-lower-alkyl or aryl-lower-alkyl, and $R_2$ or $R_1$ is hydrogen or lower alkyl.

Compounds I to be preferably emphasized are those wherein Ph is o-phenylene unsubstituted or at most di-substituted by $C_1$–$C_4$-lower alkyl, $C_1$–$C_4$-lower alkoxy, chlorine or hydroxy, $R_1$ or $R_2$ is piperidyl which optionally contains a C-C-double bond emanating from the ring-C-atom bound to the benzo[b]thienyl radical, and which at its other ring-C-atoms is unsubstituted or substituted by one methyl, and which at its N-atom is unsubstituted or substituted by $C_1$–$C_4$ -lower alkyl, $C_3$–$C_4$-lower alkenyl, $C_3$–$C_4$-lower-alkynyl, $C_3$–$C_6$-cycloalkyl-$C_1$–$C_4$-lower alkyl, benzyl, $C_1$–$C_4$-lower alkyl benzyl, $C_1$–$C_4$-lower alkoxybenzyl, halobenzyl, 2-phenethyl or α-methyl-2-phenethyl, and $R_2$ or $R_1$ is hydrogen or $C_1$–$C_4$-lower alkyl.

Compounds I to be especially emphasized are those wherein Ph is o-phenylene, $R_1$ or $R_2$ is piperidyl which optionally contains a C-C-double bond emanating from the ring-C-atom bound to the benzo[b]thienyl radical, and which at its other ring-C-atoms is unsubstituted or substituted by one methyl, and which at its N-atom is unsubstituted or substituted by $C_1$–$C_4$-lower alkyl, $C_3$–$C_4$-lower alkenyl, $C_3$–$C_4$-lower alkynyl, cyclopropylmethyl or benzyl, and $R_2$ or $R_1$ is hydrogen.

Compounds I which however are preferred most of all are those wherein Ph is o-phenylene, $R_1$ or $R_2$ is 4-piperidyl or 1,2,3,6-tetrahydro-4-pyridyl, which is unsubstituted or substituted in the 3-position by methyl, and which is substituted at its N-atom by allyl, 2-propynyl or cyclopropylmethyl or benzyl, but preferably unsubstituted or substituted by methyl, and $R_2$ or $R_1$ is hydrogen.

The compounds I and their acid addition salts can be produced by methods known per se. Thus, for instance, a. compounds I, wherein $R_1$ is the piperidyl defined under formula I, $R_2$ is hydrogen and Ph has the meaning given under formula I, are produced by a process in which a compound of formula II

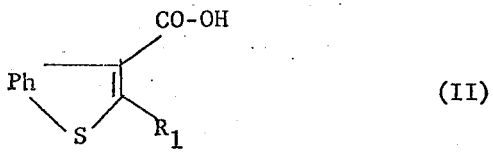

wherein $R_1$ and Ph have the meanings given under formula I, are decarboxylated; or b. compounds I, wherein the piperidyl $R_1$ or $R_2$ defined under formula I is N-unsubstituted, and Ph and $R_2$ or $R_1$ have the meanings given under formula I, are produced by a process in which in a compound III corresponding to compound I but having a cleavable radical on the piperidyl-N-atom this radical is split off; or c. compounds I, wherein the piperidyl $R_1$ or $R_2$ defined under forumla I is N-substituted, as given there, and Ph and $R_2$ or $R_1$ have the meanings given under formula I, are produced by a process in which a piperidinium compound IV, corresponding to a compound I, wherein the piperidy-N-atom is doubly bound to its substituent and carries a positive charge, or the corresponding semi-aminal, is reduced; or d. compounds I, wherein one of the radicals $R_1$ and $R_2$ is hydrogen or lower alkyl, and the other of the radicals $R_1$ and $R_2$ is optionally C-substituted piperidyl which optionally contains a C-C-double bond emanating from the ring-C-atom bound to the benzo[b]thienyl radical, and which optionally carries on the N-atom a hydrocarbon radical of aliphatic character, which radical is optionally substituted in a position higher than the 1-position, and Ph has the meaning given under formula I, are produced by a process in which a compound V, corresponding to a compound I, which compound V contains in place of the piperidyl defined under formula I a corresponding pyridyl or pyridylium, is reduced; or e. compounds I, wherein $R_1$ or $R_2$ optionally C-substituted piperidyl which carriers hydroxy on the ring-C-atom bound to the benzo[b]thienyl radical, and which carries on the N-atom a hydrocarbon radical of aliphatic character, which radical is optionally substituted in a position higher than the 1-position, and Ph and $R_2$ or $R_1$ have the meanings given under formula I, are produced by a process in which a compound of formula VI

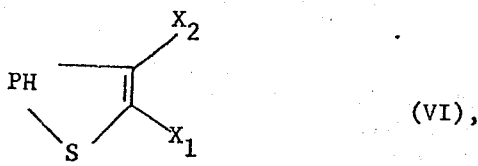

wherein Ph has the meaning given under formula I, one of the radicals $X_1$ and $X_2$ is hydrogen or lower alkyl and the other of the radicals $X_1$ and $X_2$ is a metal radical, is reacted with a compound of formula VII $$O = Pip^a \qquad (VII)$$

wherein $Pip^a$ is optionally C-substituted C-piperidylidene which carries on the N-atom a hydrocarbon radical of aliphatic character, which radical is optionally substituted in a position higher than the 1-position; or f. compounds I, wherein Ph has the meaning given under formula I, $R_2$ is hydrogen or lower alkyl, and $R_1$ is the N-substituted piperidyl given under formula I, are produced by a process wherein a compound of formula VIII

wherein Ph, $R_1$ and $R_2$ have the meanings given under formula I, $X_3$ stands for reactive esterified hydroxy, and $X_4$ is lower alkanoyl, is cyclised; or g. compounds I, wherein $R_1$ or $R_2$ is optionally C-substituted piperidyl which carries on the N-atom a hydrocarbon radical of aliphatic character, which radical is optionally substituted in a position higher than the 1-position, and Ph and $R_2$ or $R_1$ have the meanings given under formula I, are produced by a process in which a compound of formula VI

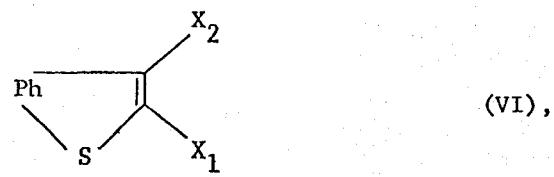

wherein Ph has the meaning given under formula I, one of the radicals $X_1$ and $X_2$ is hydrogen or lower alkyl, and the other of the radicals $X_1$ and $X_2$ is a metal radical, is reacted with a compound of formula IX $$X_5 - Pip^b \qquad (IX),$$

wherein $X_5$ is a reactive esterified hydroxy, and $Pip^b$ is optionally C-substituted piperidyl which carries on the N-atom a hydrocarbon radical of aliphatic character, which radical is optionally substituted in a position higher than the 1-position; or h. compounds I, wherein the piperidyl $R_1$ or $R_2$ defined under formula I is N-substituted, as given there, and Ph and $R_2$ or $R_1$ have the meanings given under formula I, are produced by a process in which a corresponding compound X which carries on the piperidyl-N-atom, in place of the substituent as defined, the acyl radical of the corresponding carboxylic acid or lower alkoxy carbonyl, and which in other respects corresponds to compound I, is reduced with a hydride; or i. compounds I, wherein one of the radicals $R_1$ and $R_2$ is hydrogen or lower alkyl, and the other of the radicals $R_1$ and $R_2$ is 4-piperidyl which carries on the N-atom a hydrocarbon radical of aliphatic character, which radical is optionally substituted in a position higher than the 1-position, and Ph has the meaning given under formula I, are produced by a process in which a compound of formula XI

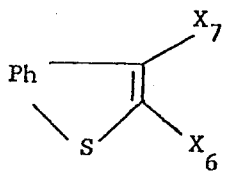

(XI), wherein Ph has the meaning given under formula I, one of the radicals $X_6$ and $X_7$ is hydrogen or lower alkyl, and the other is a radical of the partial formula XIb

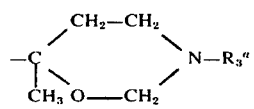

(XIb), wherein $R_3{}^a$ represents a hydrocarbon radical of aliphatic character, which radical is optionally substituted in a position higher than the 1-position, or the crude reaction product from a compound of formula XII

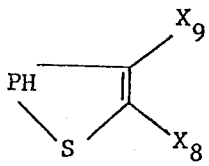

(XII), wherein one of the radicals $X_8$ and $X_9$ is hydrogen or lower alkyl, and the other of the radicals $X_8$ and $X_9$ represents the isopropenyl radical of the partial formula XIIb

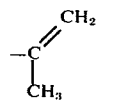

(XIIb), and Ph has the meaning given under formula I, with the double-molar amount of formaldehyde and a compound of formula XIII $$H_2N - R_3{}^a \quad (XIII),$$

wherein $R_3{}^a$ has the meaning given under the partial formula XIb, which compound is used as an addition salt of a strong acid or together with such an acid, is treated with a strong acid;

and, optionally, a compound I obtained by one of the processes given under (a) to (i) is converted into an addition salt with an inorganic or organic acid.

In the compounds I obtained, it is possible, within the limits of the definition for these compounds, to introduce, split off or modify substituents in the usual manner, i.e. to convert resulting compounds I in the usual way into other final materials I as defined. Thus, for instance, j. resulting compounds I, wherein $R_1$ or $R_2$ is optionally C-substituted piperidyl which optionally contains a C-C-double bond emanating from the ring-C-atom bound to the benzo[b]thienyl radical, or carries hydroxy on this C-atom, but which is N-unsubstituted, and Ph and $R_2$ or $R_1$ have the meanings given under formula I, are substituted on the N-atom, in a manner known per se, by a hydrocarbon radical of aliphatic character $R_3{}^a$, which radical is optionally substituted in a position higher than the 1-position, the applied procedure being, in particular, one whereby a corresponding compound I is reacted with a reactive ester of an alcohol of formula XIV $$HO - R_3{}^a \quad (XIV)$$

wherein $R_3{}^a$ represents a hydrocarbon radical of aliphatic character, which radical is optionally substituted in a position higher than the 1-position; or
a corresponding compound I is reacted, under reducing conditions, with an oxo compound of formula XV $$O = R_3{}^b \quad (XV),$$

wherein $R_3{}^b$ represents a geminally bivalent hydrocarbon radical of aliphatic character, which radical is optionally substituted in a position higher than the 1-position; or a corresponding compound I is caused to undergo an addition reaction with a compound of formula XVI

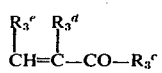

(XVI), wherein $R_3{}^c$, $R_3{}^d$ and $R_3{}^e$ represent radicals which supplement the group $-C'H - C'H - CO -$ to form a radical oxo-substituted in the 3-position and embraced by the definition for $R_3{}^a$, of which radicals two may also be bound together; or a corresponding compound I is condensed with formaldehyde and a compound of formula XVII

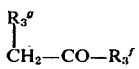

(XVII), wherein $R_3{}^f$ and $R_3{}^g$ represent separated radicals or radicals bound together, which supplement the group $- CH_2 - C'H - CO -$ to form a radical oxo-substituted in the 3-position and embraced by the definition for $R_3{}^a$; or k. in resulting compounds I, wherein $R_1$ or $R_2$ is optionally substituted C-substituted piperidyl which carries hydroxy on the ring-C-atom bound to the benzo[b]thienyl radical, and optionally carries on the N-atom a hydrocarbon radical of aliphatic character, which radical is optionally substituted in a position higher than the 1-position, and Ph and $R_2$ or $R_1$ have the meanings given under formula I, water is split off; or l. resulting compounds I having one or more non-aromatic C-C-double bonds and/or a C-C-triple bond are hydrogenated to compounds without, or with a reduced number of, non-aromatic C-C-double bonds; or m. in resulting compounds I having an α-arylalkyl radical on the piperidyl-N-atom and/or having aromatically bound α-arylalkoxy groups, the α-arylalkyl radical(s) is, or are, split off in a manner known per se; or n. in resulting compounds I, phenyl nuclei are halogenated; or o. in resulting compounds I, which contain halogen as substituent of Ph and, on the other hand, neither hydroxy nor the oxo radical as substituent of $R_3$, the halogen mentioned is replaced by a metal radical, and the resulting metal compound is reacted with an oxo-lower-alkane or with a cycloalkanone hhaving 5–10 C-atoms, of which 5–8 are ring-C-atoms; or p. in resulting compounds I having aromatically bound halogen, this is removed by catalytic hydrogenation.

As starting materials II for process (a), there are used, for example, those of formula IIa

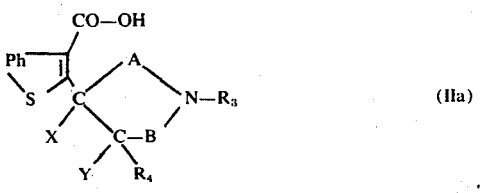

wherein Ph has the meanings given under formula I, and A, B, $R_3$, $R_4$, X and Y have the meanings given under the partial formula Io. Decarboxylation of compounds II or IIa can be performed in the usual manner; especially by heating, e.g., to a temperature of about 250°–300°C and higher, preferably in the presence of an alkaline-earth metal oxide, especially calcium oxide. It is also possible, however, to firstly convert a carboxylic acid II or IIa into an alkali metal salt or alkaline-earth metal salt, or into a copper, mercury or silver salt, and to heat this salt, e.g., to the above-mentioned temperature.

As starting materials III for process (b), there are used, for example, those of formula IIIa

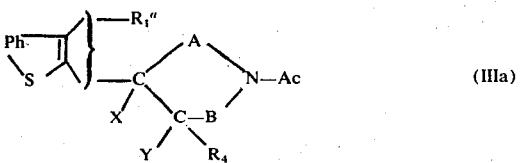

wherein
Ac represents a cleavable radical, and
$R_1^a$ represents hydrogen or lower alkyl, and
Ph has the meaning given under formula I, and A, B, $R_4$, X and Y have the meanings given under formula Io. the splitting-off of the cleavable Ac, which is preferably an acyl radical, can be performed in a manner known per se, especially in the usual way by solvolysis, such as basic or acid hydrolysis, or by reduction.

Acyl radicals that can be split off by hydrolysis are, e.g., optionally functionally modified carboxyl groups, for example, oxycarbonyl radicals such as lower-alkoxycarbonyl radicals, e.g., the tert.-butoxycarbonyl radical or the ethoxycarbonyl radical, aralkoxycarbonyl radicals such as phenyl-lower-alkoxycarbonyl radicals, e.g., a benzyloxycarbonyl radical, halocarbonyl radicals, e.g., the chlorocarbonyl radical, also arylsulphonyl radicals such as toluenesulphonyl radicals or bromobenzenesulphonyl radicals, and optionally halogenated such as fluorinated, acyl radicals of organic carboxylic acids, such as lower alkanoyl radicals, e.g., the formyl, acetyl or trifluoroacetyl radical, or a benzoyl radical, also cyano groups, or silyl radicals such as tri-lower-alkylsilyl radicals, e.g., the trimethylsilyl radical, as well as functionally modified thiocarbonyl groups, such as lower-alkoxy-thiocarbonyl radicals, e.g., methoxy-thiocarbonyl, or lower-alkylthio-thiocarbonyl radicals, e.g., methylthio-thiocarbonyl.

Hydrolysis can be performed in the usual manner, e.g. in the presence of hydrolysing agents, for example, in the presence of acid agents, such as aqueous mineral acids such as sulphuric acid or hydrohalic acid, or in the presence of basic agents, e.g., alkali hydroxides such as sodium hydroxide. For example, hydrolysis is effected by prolonged heating with an alkali hydroxide, especially sodium or potassium hydroxide, in a hydroxy compound in the presence of a small amount of water at a temperature of between about 80° and 200°C. A suitable reaction medium is, for example, ethylene glycol, or a lower monoalkyl ether thereof, and, where hydrolysis is performed in a closed vessel, also a lower alkanol such as methanol, ethanol or butanol. It is moreover possible to hydrolyse compounds of the general formula II, particularly those wherein Ac represents a cyano group, i.e. the acyl radical of cyanic acid, or a chlorocarbonyl group, also by heating with a mineral acid in an organic-aqueous or aqueous medium, e.g., by boiling for several hours in a mixture of 85% phosphoric acid and formic acid, or by several hours' heating in 48% hydrobromic acid or in a hydrobromic acid/acetic acid mixture at about 60°– 100°C, preferably at 60°–70°C. Furthermore, it is possible to split off, for example, a tert.-butoxycarbonyl radical, under anhydrous conditions, by treatment with a suitable acid, such as trifluoroacetic acid.

Further groups Ac that can be split off by hydrolysis are the groups formed by addition of a methyl group in the place of Ac to azodicarboxylic acid di-lower-alkyl esters, which groups are split off preferably by hydrolysis in an acid medium, particularly by boiling in dilute, e.g., 1N, hydrochloric acid, with liberation of hydrazodicarboxylic acid-di-lower-alkyl esters.

Radicals that can be split off by reduction, especially acyl radicals, are, for example, α-aralkoxycarbonyl radicals, such as benzyloxycarbonyl radicals, which can be split off in the usual manner by hydrogenolysis, particularly by catalytically activated hydrogen, such as by hydrogen in the presence of a hydrogenation catalyst, for example, a platinum or palladium catalyst, or Raney nickel. Further radicals that can be split off by reduction are, for example, 2-halo-alkoxycarbonyl radicals, such as the 2,2,2-trichloroethoxycarbonyl radical or the 2-iodoethoxy- or 2,2,2-tribromoethoxycarbonyl radical, which can be split off in the usual manner, especially by metallic reduction (so-called nascent hydrogen). Nascent hydrogen can be obtained by the action of metal or metal alloys, such as amalgams, on agents releasing hydrogen, such as carboxylic acids, alcohols or water, with, in particular, zinc or zinc alloys together with acetic acid being suitable. The reduction of 2-halo-alkoxycarbonyl radicals can also be performed by means of chromium(II)-compounds, such as chromium(II)-chloride or chromium(II)-acetate.

An acyl radical that can be split off by reduction can also be a sulphonyl group such as a lower-alkanesulphonyl group, or arylsulphonyl group such as methanesulphonyl or p-toluenesulphonyl, which can be split off in the usual manner by reduction with nascent hydrogen, e.g., by an alkali metal such as lithium or sodium, in liquid ammonia; or it can also be electrolytically split off.

The starting materials for process c) correspond, for example, to formula IVa or IVb

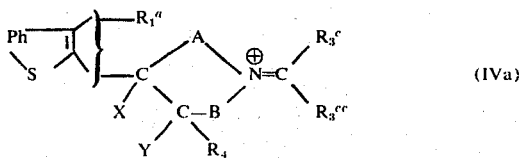

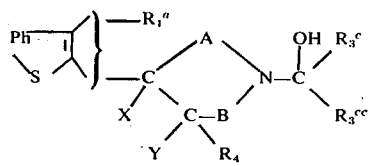

(IVb)

wherein $R_3{}^c$ represents hydrogen or a monovalent, optionally substituted hydrocarbon radical, and $R_3{}^{cc}$ represents hydrogen or lower alkyl, or $R_3{}^c$ and $R_3{}^{cc}$ together represent a bivalent, optionally substituted hydrocarbon radical, and $R_1{}^a$ represents hydrogen or lower alkyl, and Ph has the meaning given under formula I, and A, B, $R_4$, X and Y have the meanings given under the partial formula Io.

The reduction according to (c) can be carried out in the usual manner; for example, with formic acid, with a bilight metal hydride, such as an alkali metal boron hydride or alkali metal aluminium hydride, e.g., lithium-aluminium hydride, with a hydride such as diborane, or with hydrogen in the presence of a hydrogenating catalyst, for example, a noble metal catalyst such as a platinum or palladium catalyst, or a nickel catalyst or alloy-skeleton catalyst such as Raney nickel.

As starting materials for process (d), there are used, for example, those of the general formula Va or Vb

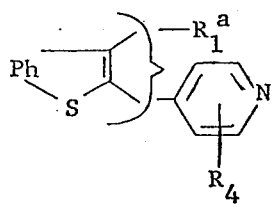

(Va)

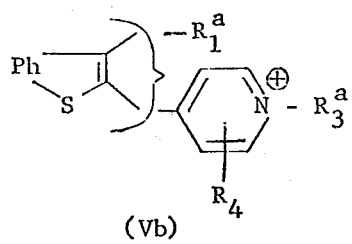

(Vb)

wherein $R_1{}^a$ represents hydrogen or lower alkyl, and $R_3{}^a$ represents a hydrocarbon radical of aliphatic character, which radical is optionally substituted in a position higher than the 1-position, and Ph has the meaning given under formula I, and $R_3$ and $R_4$ have the meanings given under the partial formula Io. The production of the required starting materials is described later on in the text.

The reduction can be performed in a known manner. If it is required to obtain compounds I wherein the piperidyl $R_1$ or $R_2$ is completely hydrogenated, or the symbols X and Y of the partial formula Io represent hydrogen, then reduction is carried out to completion.

Pyridyl and Pyridylium compounds V or Va and Vb can, in particular, be reduced in the usual manner by catalytic hydrogenation, with corresponding piperidyl compounds I being obtained after exhaustive hydrogenation.

The catalytic hydrogenation of pyridyl and pyridylium compounds V or Va and Vb can be performed with the use of conventional hydrogenation catalysts; for example, with the use of noble metal catalysts such as palladium on charcoal, or platinum oxide, rhodium catalysts such as rhodium on charcoal or on aluminium oxide, or alloy-skeleton catalysts such as Raney nickel, in an inert organic solvent such as methanol, ethanol or dioxane, at room temperature and at normal pressure, or at moderately elevated temperature up to about 100°C and at elevated pressure up to about 100 bars.

If it is required to obtain compounds I wherein the piperidyl $R_1$ or $R_2$ contains a C-C-double bond emanating from the C-atom bound to the benzo[b]thienyl radical, or the symbols X and Y of the partial formula Io together represent an additional bond, then the reduction is only partially carried out.

The partial reduction of pyridylium compounds V or Vb is performed preferably with the aid of sodium or potassium boron hydride in organic-aqueous medium, the procedure being, for example, that there is slowly added to the prepared solution of the starting material V or Vb in an organic, water-miscible solvent, e.g., in a lower alkanol such as methanol or ethanol, or in mixtures thereof with water, an aqueous solution of sodium boron hydride, and the reaction mixture is subsequently allowed to further react for some time, whereby a reaction temperature of, e.g., between about 5° and 60°C, preferably between room temperature and 35°C, is maintained. If the starting materials are 2- or 3-(4-pyridylium)-compounds V or Vb, then there are obtained compounds I having a 1,2,3,6-tetrahydro-4-pyridyl radical in the 2- or 3-position. If the starting materials are 2- or 3-(3-pyridylium)-compounds V or Vb, then there are obtained compounds I having a 1,2,5,6-tetrahydro-3-pyridyl radical in the 2- or 3-position. If the starting materials are 2- or 3-(2-pyridylium)-compounds V or Vb, then there are obtained compounds I having a 1,4,5,6-tetrahydro-2-pyridyl radical in the 2- or 3-position.

In the starting materials of formula VI for process e), a metal radical $X_1$ or $X_2$ is a monovalent radical of a metal compound or of a metal, such as of a magnesium compound, e.g., of a magnesium-halogen compound, such as -MgCl, -MgBr or -MgJ, or, in particular, of an alkali metal, particularly lithium. The production of such starting materials is described later on in the text.

As starting materials of formula VII, there are used, for example, those of the formula VIIa

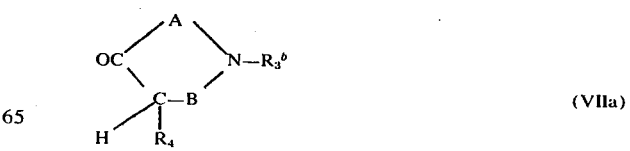

(VIIa)

wherein $R_3$ represents a hydrocarbon radical of aliphatic character which optionally carries inert substituents in a position higher than the 1-position, and $R_4$, A and B have the meanings given under the partial formula Io. Inert substituents of $R_3{}^b$ are, in particular, lower alkoxy and aromatically bound halogen.

The reaction according to e) can be performed in a manner known per se, particularly in an inert solvent, such as an ether, e.g., diethyl ether or tetrahydrofuran, and advantageously in an inert-gas atmosphere, e.g., under nitrogen or argon. The reaction is performed, for example, at a temperature of between about −80°C and +25°C, if necessary also at a slightly elevated temperature, preferably at the boiling temperature of the solvent. After completed reaction, the reaction mixture is slowly decomposed with water or, e.g., with an aqueous base, and the reaction product is isolated in a manner known per se.

In the starting materials of formula VIII for the cyclisation according to (f), reactive esterified hydroxy $X_3$ is one that has been esterified with a strong acid, e.g. with a hydrohalic acid, such as hydrobromic acid. Thus, $X_3$ stands, in particular, for bromine.

Lower alkanoyl $X_4$ is, e.g., propionyl and especially acetyl.

The cyclisation can be performed in a manner known per se, especially with a strongly alkaline condensation agent, such as sodium hydride, potassium hydroxide, or alkali alkanolate such as sodium- or potassium-lower-alkanolate, e.g., sodium ethanolate or potassium ethanolate, sodium isopropanolate or potassium isopropanolate, or sodium tert.-butanolate or potassium tert.-butanolate. In the case of sodium hydride, cyclisation is advantageously performed in a solvent such as an ether, e.g. tetrahydrofuran or dioxane. In the case of, e.g., potassium hydroxide, it is advantageously performed in a solvent such as a lower alkanol, e.g. ethanol, isopropanol or water. The production of starting materials of formula VIII is described later on in the text.

The reaction according to (g) can be carried out by a process analogous to process (e). In the starting materials of formula VI used for this purpose, $X_1$ and $X_2$ preferably have the aforementioned meaning. As compounds of formula IX, there are used, for example, those of formula IXa

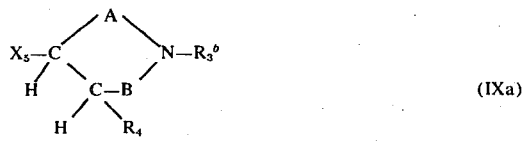

wherein
$R_3{}^b$ represents a hydrocarbon radical optionally carrying inert substituents in a position higher than the 1-position,
$X_5$ has the meaning given under formula IX, and $R_4$, A and B have the meanings given under the partial formula Io. Inert substituents of $R_3{}^b$ are, in particular, lower alkoxy and aromatically bound halogen. The reactive esterified hydroxy $X_5$ is, in particular, hydroxy esterified by hydrogen halide, such as chlorine, bromine or iodine, also hydroxy esterified by organic sulphonic acids, especially lower-alkanesulphonic acids or arenesulphonic acids, such as, e.g., methanesulphonyloxy or p-toluenesulphonyloxy. A preferably has 2 to 3 chain members. Accordingly, B possesses one single chain member or constitutes a direct bond.

As compounds X for the reduction according to (h), there are used, in particular, those of formula Xa

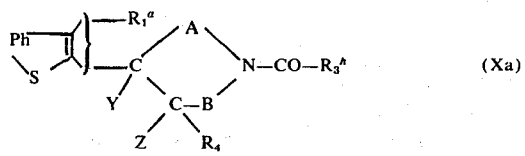

wherein
$R_1{}^a$ represents hydrogen or lower alkyl, and
$R_3{}^h$ represents a radical lessened by methylene, corresponding to the definition for $R_3$ given under the partial formula Io, or lower-alkoxycarbonyl, and
Ph has the meaning given under formula I, and $R_4$, A, B, Y and Z have the meanings given under the partial formula Io.

The reduction of the amide group of compounds X or Xa is performed, for example, by means of lithium aluminium hydride or diborane in an ethereal solvent, such as diethyl ether, tetrahydrofuran, dibutyl ether or diethylene glycol diethyl ether, or mixtures thereof, at a temperature of between about 20° and 100°C or the boiling temperature of the employed reaction medium, where this is below 100°C. The diborane can either be prepared separately and then introduced, or be formed in situ from sodium boron hydride and boron trifluoride etherate.

In the case of process ei), the strong acid employed is preferably a mineral acid such as hydrochloric acid, especially concentrated hydrochloric acid, or sulphuric acid, particularly moderately diluted 66% sulphuric acid. After initial cooling for the control of the exothermic reaction, the reaction temperature is between 60° and 110°C, preferably 90°–100°C, with a reaction duration of about 1 to 10 hours, preferably 5-6 hours.

The starting materials of formula XI, together with 1-substituted 4-(benzo[b]thien-2- or -3-yl)-piperidinoles embraced by formula I, are formed on reaction of compounds of formula XII with the doublemolar amount of formaldehyde, for example, as a ca. 35% aqueous solution, and the equimolar amount of a mineral-acid salt, especially the hydrochloride, of a compound of formula XIII, and are hence also contained in the crude reaction products usable in place of compounds of formula XI. These crude reaction products are produced essentially under the same reaction conditions as those under which the subsequent process (i) is performed; but there is used an amount of a strong acid, such as concentrated hydrochloric acid, that is merely equinormal with respect to the compound of formula XIII, provided that it is not preferred to use the compound of formula XIII as an acid addition salt, preferably as hydrochloride. In order to subsequently effect the conversion of the formed compound of formula XI and, at the same time, dehydration of the piperidinol concomitantly formed, it is then only necessary to gradually add, with cooling, e.g., at 50°–70°C, a further amount of mineral acid, such as concentrated sulphuric acid, and to complete the reaction by heating at, e.g., 90°–95°C. By applying a variant of the process — which in most cases is less advantageous — it is possible to carry out the formation of the crude reaction product and the conversion and dehydration therof simultaneously, the procedure of the variant being such that there is used from the commencement an excess of a strong acid, particularly of sulphuric acid or hydrochloric acid. Compounds of formula XII are obtainable, for example, by reaction of compounds of formula VI or VIa with acetone in a manner known per se.

The compounds I suitable for reactions according to (j) correspond preferably to formula Ij

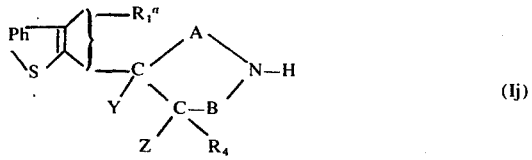

(Ij)

wherein $R_1^a$ represents hydrogen or lower alkyl,

Ph has the meaning given under formula I, and $R_4$, A, B, Y and Z have the meanings given under partial formula Io.

Suitable reactive esters of compounds of formula XIV for the reaction with compounds of formula I or Ij according to process (j) are, for example, esters of hydrohalic acid, especially chlorides, bromides and iodides, also lower alkanesulphonic acid esters and arenesulphonic acid esters, such as methanesulphonic acid esters, or benzenesulphonic acid esters and p-toluenesulphonic acid esters, as well as esters of other strong acids, e.g., sulphuric acid esters such as dimethylsulphate and diethylsulphate. The reactions with compounds of formula I and Ij are performed preferably in the presence of an acid-binding agent in an organic solvent inert under the reaction conditions. Suitable acid-binding agents are tertiary organic bases, such as, e.g., triethylamine, pyridine, sym. collidine and, in particular, ethyldiisopropylamine, or inorganic basic substances, such as, e.g. sodium carbonate or potassium carbonate; and suitable solvents are, e.g., lower alkanols such as methanol, ethanol, isopropanol or butanol, ethereal compounds such as dioxane, tetrahydrofuran or 2-methoxyethanol, lower aliphatic ketones such as methyl ethyl ketone, and N-substituted acid amides such as dimethylformamide or N,N,N',N',-N'',N''-hexamethylphosphoric acid-triamide. The reaction temperature is between about 0° and 200°C, preferably between room temperature and about 120° C. The reaction temperatures required for reactions with reactive esters of primary hydroxy compounds are in most cases at the lower limit of the given ranges, whereas reaction with reactive esters of nonprimary hydroxy compounds have usually to be performed at higher temperatures and consequently in closed reaction vessels if necessary, with the use of a particularly effective acid-binding agent, such as ethyldiisopropylamine, being of advantage.

The reactions of compounds of formula I or Ij with oxo compounds of formula XV are performed, for example, in formic acid at a temperature of between about 70° and 100°C; or optionally by the action of hydrogen in the presence of a hydrogenation catalyst, such as Raney nickel, platinum oxide or palladium charcoal, at normal or moderately elevated pressure and temperature, in a suitable organic solvent, such as ethanol or dioxane. Suitable oxo compounds are, for example, aliphatic aldehydes having at least 2 carbon atoms, aliphatic and cycloaliphatic ketones, benzaldehyde and substituted benzaldehydes as defined. Most suitable, however, is formaldehyde, which is preferably used together with formic acid as reducing agent.

The addition of compounds of formula I or Ij to unsaturated oxo compounds of formula XVI is performed, for example, in an inert organic solvent, such as benzene, at room temperature, or if necessary with heating. In the starting materials of formula XVI, preferably at least one of the symbols $R_3^d$ and $R_3^e$ represents hydrogen; however, compounds being characterised by having good reactivity and being easily producible are those in which both symbols represent hydrogen.

The condensation of compounds of formula I or Ij with formaldehyde and a compound of the general formula XVII can be performed under the usual conditions of the Mannich reaction, e.g. by heating of the hydrochloride of a compound of formula I or Ij with formaldehyde, which is employed as aqueous solution or as paraformaldehyde, and preferably in excess, in an organic solution to a temperature of between about 70° and 140°C or the boiling temperature of the reaction medium should this temperature be below 140°C. Suitable solvents are, in particular, lower alkanols, such as ethanol, methanol, isopropanol, butanol or isopentanol, as well as other, preferably water-miscible, solvents, such as dioxane.

Reactive agents of hydroxy compounds of formula XIV, oxo compounds of formula XV as well as compounds of formulae XVI and XVII are known in appreciable numbers, and others are obtainable by processes analogous to those for obtaining the known compounds. The starting materials of formula I or Ij can in general be produced by the processes mentioned in the foregoing. An advantageous manufacturing process for compounds of formula Ij in which Y and Z denote hydrogen atoms is, for example, the reduction of compounds V or Va.

Compounds of formula I suitable for splitting off water according to k) correspond, for example, to formula Ik

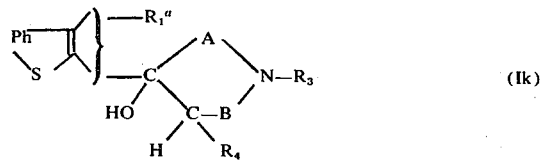

(Ik)

wherein $R_1^a$ represents hydrogen or lower alkyl, Ph has the meaning given under formula I, and $R_3$, $R_4$, A and B have the meanings given under partial formula Io. Preferably, $R_3$ has a meaning other than hydrogen, and A possesses 2 to 3 chain members, whilst B accordingly contains a single chain member or represents a direct bond. The splitting-off of water can be performed in a manner known per se, especially by heating and, advantageously, with separation of the formed water, advantageously also in the presence of a strong acid, e.g., sulphuric acid, which can be used concentrated but in small quantities. The splitting-off of water can be performed also in an inert solvent, e.g., in a solvent not miscible with water, such as benzene, toluene or xylene, and advantageously with separation of water.

Hydrogenation according to (1) can on the one hand be a hydrogenation of the cyclic double bond emanating from the C-atom of piperidyl, which C-atom is bound to the benzo[b]thienyl radical, and, on the other hand, the sole or additional hydrogenation of a non-aromatic double bond present at another position of a corresponding compound of formula I, of a triple bond or of several such double bonds. Suitable for the first-mentioned hydrogenation are, quite generally, compounds of formula I in which $R_1$ or $R_2$ is a radical of the partial formula Io wherein Y and Z together represent an additional bond. Suitable for the last-mentioned hydrogenation are compounds of formula I having a radical of the partial formula Io as $R_1$ or $R_2$, in which compounds $R_3$ contains one or more non-aromatic double bonds or a triple bond, whilst Y and Z each represent hydrogen atoms, or together they represent an additional bond, which is optionally simultaneously hydrogenated.

Hydrogenation can be performed in the usual manner in the presence of a hydrogenation catalyst, for example, a noble metal catalyst such as a platinum or palladium catalyst, or a nickel catalyst or alloy-skeleton catalyst such as Raney nickel. Care must be taken in this process to make certain that other reducible groups are not attacked. Thus, in the case of, in particular, hydrogenation with hydrogen in the presence of Raney nickel, it is to be ensured that optionally present halogen atoms bound to aromatic rings are not replaced by hydrogen. Sulphur-resistant catalysts are preferably to be used, and, where required, the hydrogen absorption is to be volumetrically recorded and hydrogenation terminated after absorption of the calculated amount of hydrogen. Compounds having a C-C-double bond are, for example, hydrogenated as such, or in the form of their hydrochloride, at normal pressure and at room temperature, or at slightly elevated pressures and/or temperatures, in a lower alkanol, such as methanol.

The splitting-off of an α-arylalkyl radical on the piperidyl-N-atom, and/or the splitting of aromatically bound α-arylalkoxy groups according to process (m), can be performed, for example, by hydrogenolysis. Hydrogenolysis can be performed essentially under the reaction conditions given for the above-mentioned process (1), and with use of the catalysts mentioned there. The hydrogenolysis can therefore be carried out in the same operation as a hydrogenation according to (1); on the other hand, however, the selective hydrogenation of the double bond of the piperidyl radical, which double bond emanates from the C-atom bound to the benzo[b]thienyl radical, is easily performed. According to a second variant of process (m), the splitting-off or splitting of the aforementioned radical is performed in an acid medium, e.g., by heating in a mixture of hydrobromic acid and acetic acid at a temperature of between about 50°C and the boiling temperature of the mixture. The α-arylalkyl radicals or α-arylalkoxy radicals are, for example, benzyl radicals or benzyloxy radicals, which can contain substituents that do not unfavourably affect, but preferably accelerate, the course of splitting. For example, the p-methoxybenzyl group and the p-methoxybenzyloxy group can be split off and split, respectively, in acid medium other conditions milder than those in the case of the corresponding unsubstituted groups.

The halogenation of phenyl nuclei according to process (n), especially the introduction of a chlorine or bromine atom into the 5-position of the benzo[b]thiophene ring system, can be effected in the usual manner, preferably at non-elevated temperature, or with cooling, and in the presence of a catalyst, such as iron, iodine, iron(III)-chloride or aluminium chloride, or the corresponding bromides.

In the compounds I suitable as starting materials for the process according to (o), there is present as halogen in radical Ph, for example, chlorine or, in particular, bromine, preferably in the 5-position. This halogen is converted, for example, by means of activated magnesium into a chloromagnesium or bromomagnesium radical, or replaced, by means of an alkali aromatically compound such as butyllithium, by an alkali metal radical, particularly the lithium radical, with the employed solvent being, for example, an ether or an ethereal solvent, such as diethyl ether or tetrahydrofuran. In the same medium or optionally with the addition of an inert solvent such as benzene, it is also possible to perform the subsequent reaction with the oxo-loweralkane or with the cycloalkanone as defined, for example, at a temperature of between −10°C and the boiling temperature of the reaction medium.

The catalytical hydrogenation according to (p) for the splitting-off of aromatic bound halogen can be performed in the presence of conventional hydrogenation catalysts, such as Raney nickel, or palladium on charcoal.

The reaction mentioned can optionally be performed simultaneously, or successively in any chosen sequence.

The stated reactions are carried out in the usual manner in the presence or absence of diluents, condensation agents and/or catalytic agents, at a lowered temperature, at the normal temperature or at elevated temperature, and if necessary in a closed vessel.

Depending on the process conditions and starting materials, the final materials I are obtained in the free form, or in the form, likewise embraced by the invention, of their acid addition salts. Thus, there can be obtained, for example, basic, neutral or mixed acid addition salts, optionally also hemi-, mono-, sesqui-or polyhydrates thereof. The acid addition salts of the new compounds can be converted, in a known manner, into the free compound, e.g., with basic agents, such as alkalies or ion exchangers. On the other hand, the free bases obtained can form salts with organic or inorganic acids. For the preparation of acid addition salts, there are used, in particular, those acids which are suitable for the obtainment of pharmaceutically acceptable acid addition salts. Such acids are, for example: hydrohalic acids, sulphuric acids, phosphoric acids, nitric acid, fumaric acid, aliphatic, alicyclic, aromatic or heterocyclic carboxylic or sulphonic acids, such as formic, acetic, propionic, succinic, glycolic, lactic, malic, tartaric, citric, ascorbic, maleic, pyruvic, benzoic, anthranilic, p-hydroxybenzoic, salicyclic, pamoic, methanesulphonic, ethanesulphonic, hydroxyethanesulphonic, ethylenesulphonic, halobenzenesulphonic, toluenesulphonic, cyclohexylaminesulphonic or sulphanilic acid.

These or other acid addition salts of the new compounds I, such as picrates or perchlorates, can also serve for purification of the free bases obtained, in that the free bases are converted into salts, these are separated, and the bases are then liberated from the salts. In consequence of the close relationship between the new compounds in the free form and in the form of their salts, it is to be taken, in the foregoing and in the following, that by the term 'free compounds' is meant, where the case applies and with the appropriate modifications, also the corresponding salts.

The invention relates also to those modifications of the processes whereby a compound occurring as an intermediate at some stage is used as the starting material, and the uncompleted steps are performed, or whereby the process is interrupted at some stage, or whereby a starting material is formed under the reaction conditions, or whereby a reaction constituent is optionally present in the form of its salts. For the obtainment of optically active compounds, it is possible to use optically active starting materials.

Depending on the choice of starting materials and working procedures, the new compounds can be present as racemates or optical antipodes or, provided that they have at least two asymmetrical carbon atoms, also as mixtures of diastereomers (racemate mixtures).

The mixtures of diastereomers (racemate mixtures) obtained can, by virtue of the physicochemical differences in the constituents, be separated in a known manner into the two stereoisomeric (diastereomeric) pure racemates, e.g. by chromatography and/or fractional crystallisation.

Resulting racemates can be resolved by known methods into the optical antipodes. For example, this is performed by recrystallisation from an optically active solvent, or with the aid of microorganisms; in particular, however, by reaction with an optically active forming salts with the racemic mixture, separation of the salts obtained in this manner, e.g., by virtue of their different degrees of solubility, into the individual diastereomeric salts, and liberation of the optical antipodes from these salts by the action of suitable agents, especially inorganic bases or strong organic bases. Particularly suitable optically active acids are, for example, the D- and L-forms of tartaric acid, di-o-toluyltartaric acid, malic acid, mandelic acid, camphorsulphonic acid or quinic acid. It is advantageous to isolate the more effective of the two anipodes.

For the carrying out of the reactions of the invention, there are advantageously used those starting materials which lead to the obtainment of the initially specially mentioned groups of final materials and, in particular, the specifically described or emphasised final materials.

The starting materials are known or can, if they are new, be obtained by methods known per se. Thus, starting materials II can be obtained in a manner known per se; e.g., by ring closure of α-(pyridylcarbonyl)- or α-(pyridiniumcarbonyl)-α-[o-(lower-alkylthio)-phenyl]-acetonitrile, followed by hydrolysis and subsequent reduction. Ring closure can be performed, e.g., in acid medium, after the above-mentioned nitriles have first been converted, e.g., with an alkali amide or alkali hydride, such as with sodium hydride, preferably in a solvent such as dioxane, into an alkali metal derivative. It is possible, for example, to cyclise with hydrobromic acid at elevated temperature, with the nitrile group being simultaneously hydrolysed. The reduction can be carried out analogously to process (d). Starting materials III can be obtained, in a manner known per se, from corresponding pyridinium compounds which carry on the ring nitrogen atom an acyl radical, analogously to compounds II; or, for example, likewise in a manner known per se, from corresponding tetrahydropyridine or piperidine compounds I having a methyl or benzyl group on the ring nitrogen atom, by the action of a suitable acyl halide, especially by the action of a carbonic acid or thiocarbonic acid semi-ester halide or of a cyanogen halide. Starting materials IV can be obtained, in a manner known per se, by reaction of compounds I with an unsubstituted ring nitrogen atom and corresponding ketones or aldehydes. Starting materials V can be obtained, in a manner known per se, from o-mercaptobenzaldehydes and 4-(chloromethyl)- or 2-(chloromethyl)-pyridines or -pyridinium compounds with subsequent ring closure; or from compounds VI with bromopyridine or bromopyridinium compounds. Starting materials VI are obtained, for example, in a manner known per se, from the corresponding halogen compounds, such as bromine compounds, and metal, for example, lithium. Compounds VIII can be obtained, in a manner known per se, from corresponding compounds containing hydrogen in the position of $X_3$, e.g., by reaction of such compounds with bromine in glacial acetic acid. Starting materials X can in general be produced, in a manner known per se, by N-acylation of corresponding compounds I which carry hydrogen on the ring nitrogen atom, and in some cases also by reaction of suitable carboxylic acid halides with corresponding compounds I which are substituted on the ring nitrogen atom by methyl, allyl or benzyl, with liberation of the corresponding methyl, allyl or benzyl halide. The production of compounds XI and XII has been mentioned earlier in the text. Of the starting materials VII, IX, XII, XIV, XV, XVI and XVII, some representatives are known, and others can be produced analogously.

The new compounds I can be used as pharmaceutical active substances, e.g., in the form of pharmaceutical preparations which contain them or their pharmaceutically acceptable acid addition salts in admixture with an organic or inorganic, solid or liquid, pharmaceutical carrier material that is suitable, for example, for enteral or parenteral administration. For the formation of this carrier material, suitable substances are ones which do not react with the new compounds, such as water, gelatine, lactose, starch, magnesium stearate, talcum, vegetable oils, benzyl alcohols, gum, polyalkylene glycols, vaseline, cholesterol or other known carriers for pharmaceutical active substances. The pharmaceutical preparations can be in the form of, for example, tablets, dragees, capsules, suppositories, ointments or creams, or they can be in liquid form as solutions (e.g., as elixir or syrup), suspensions or emulsions. They are optionally sterilised and/or contain auxiliaries, such as preservatives, stabilisers, wetting or emulsifying agents, salts for regulation of the osmotic pressure, or buffers. They may also contain other therapeutically valuable substances. The said preparations, which can also be used in veterinary medicine, are manufactured by the usual methods.

The daily dose for warm-blooded animals is between about 0.2 and 10 mg/kg.

The following examples illustrate the invention without, however, limiting its scope. The temperatures are given in 0°C.

EXAMPLE 1

430 ml of a 1.4N solution of n-butyllithium in absolute diethyl ether is added dropwise within 45 minutes, at a reaction temperature of −5°, to a solution of 46.5 g of benzo[b]thiophene in 300 ml of absolute diethyl ether. The solution is thereupon stirred for 1 hour at 0°. There is then added dropwise, in the course of 30 minutes, a solution of 90 g of 1-methyl-4-piperidone in 150 ml of absolute diethyl ether. The reaction temperature is held at 0° by external cooling. The reaction solution is stirred for a further 15 hours at room temperature; it is then poured with stirring onto 200 g of ice, and the aqueous phase is extracted three times with 500 ml of ethyl acetate each time. The combined organic extracts are dried by means of sodium sulphate, filtered with suction and concentrated by evaporation. The residue is dissolved in 500 ml of 2N hydrochloric acid, and the acid solution is washed with ether. The aqueous solution is afterwards brought to pH 12 by the addition of 10% sodium hydroxide solution, and extracted with one litre of chloroform. The chloroform solution is dried with sodium sulphate, filtered off with suction, and concentrated by evaporation to obtain crude 1-methyl-4-(benzo[b]thien-2-yl)-4-piperidinol. The free base melts at 161° – 163° after recrystallisation from acetone. The hydrochloride is produced with hydrogen chloride in ethyl acetate and recrystallised from acetone, whereupon it melts at 208°–210°.

EXAMPLE 2

60 g of 1-methyl-4-(benzo[b]thien-2-yl)-4-piperidinol is refluxed in 250 ml of glacial acetic acid and 70 ml of hydrochloric acid for 6 hours. The solution is cooled to room temperature, and the precipitated salt is filtered off under suction. The crystals are suspended in chloroform and washed with 2N sodium hydroxide solution. The organic phase is dried with sodium sulphate, filtered, and concentrated by evaporation. The evaporation residue is fractionally distilled in high vacuum. The fraction distilling at 160°–165° and 0.22 Torr is 1-methyl-4-(benzo[b]thien-2-yl)-1,2,3,6-tetrahydropyridine. The base melts at 135°–137° after recrystallisation from hexane. The hydrochloride produced with a solution of hydrogen chloride in ethyl acetate melts at 263° after recrystallisation from acetone.

EXAMPLE 3

17.6 g of 1-methyl-4-(benzo[b]thien-2yl)-1,2,3,6-tetrahydropyridine is dissolved in 180 ml of methanol, and hydrogenated in the presence of 14 g of palladium charcoal (5%) at a temperature of 35°–40° under normal pressure. After 42 hours, hydrogenation is interrupted with the level of hydrogen absorption at 100%; the catalyst is filtered off and the filtrate is concentrated in vacuo. The residue is fractionally distilled in high vacuum. The fraction distilling at 130° to 135° under 0.14 Torr is 1-methyl-4-(benzo[b]thien-2-yl)-piperidine. The base melts at 96°–98° after recrystallisation. The hydrochloride prepared with a solution of hydrogen chloride in ethyl acetate melts at 268°–270° after recrystallisation from acetone.

EXAMPLE 4

The whole amount of 4-(benzo[b]thien-2-yl)-1-piperidine carboxylic acid ethyl ester obtained as crude product according to Example 4a) is dissolved in 130 ml of ethylene glycol. After the addition of 15 g of solid potassium hydroxide, the resulting cloudy solution is heated, with vigorous stirring, for 15 hours at 160°. The reaction solution is thereupon cooled to 20°, and extracted three times with 500 ml of ethyl acetate each time. The organic phases are washed 5 times with one litre of water each time; they are then dried with sodium sulphate, filtered and concentrated by evaporation. The residue is dissolved in 500 ml of 2N hydrochloric acid, and the acid solution is extracted with toluene. The aqueous solution is thereupon brought to the pH-value of 12 by the addition of 10% sodium hydroxide solution, and extracted with one litre of chloroform. The chloroform solution is dried with sodium sulphate, filtered, and concentrated by evaporation to obtain crude 4-(benzo[b]thien-2-yl)-piperidine. The base melts at 82°–84° after recrystallisation from di-isopropyl ether. The hydrochloride is prepared with hydrogen chloride in ethyl acetate, and recrystallised from acetone, whereupon it melts at 220°–222°.

The 4-(benzo[b]thien-2-yl)-1-piperidinecarboxylic acid ethyl ester is produced as follows:

a. 13 g of 1-methyl-4-(benzo[b]thien-2-yl)-piperidine is dissolved in 150 ml of toluene. At a reaction temperature of 50°, 22 g of chloroformic acid ethyl ester is slowly added dropwise under a fairly strong flow of nitrogen. The solution is subsequently stirred for 20 hours at 50°; there is then added dropwise a further 11 g of chloroformic acid ethyl ester, and stirring is continued for 2 hours at 50°. The excess chloroformic acid ethyl ester if thereupon distilled off under normal pressure; the solution is cooled to 70°, filtered off with suction, and the filter residue is afterwashed with 500 ml of toluene. The combined filtrates are successively washed with 500 ml of water, 1 litre of a 10% solution of methanesulphonic acid in water, 500 ml of water, 500 ml of 2N sodium hydroxide solution and 500 ml of water; they are dried by means of sodium sulphate, filtered and concentrated by evaporation. The resulting crude 4-(benzo[b]thien-2-yl)-1-piperidinecarboxylic acid ethyl ester can be further processed without additional purification.

EXAMPLE 5

4.8 g of 4-(benzo-[b]thien-2-yl)-piperidine and 4.0 g of 3-bromopropyne are stirred in 200 ml of methanol, after the addition of 200 g of potassium carbonate, for 48 hours at room temperature. The reaction solution is then filtered off with suction; the filter residue is washed with 500 ml of chloroform, and the combined filtrates are concentrated in vacuo. The residue is dissolved in a small amount of methylene chloride, and chromatographed on 200 g of aluminium oxide (activity II, neutral). the first fractions, extracted with in all one litre of methylene chloride, contain 1-(2-propynyl)-4-(benzo[b]thien-2-yl)-piperidine. The hydrochloride prepared with a solution of hydrogen chloride in ethyl acetate is recrystallised from ethyl acetate and melts at 229°–232°.

EXAMPLE 6

In an analogous manner to that described in Example 1 there is obtained, with the use of 21.1 g of benzo[b]-thiophene in 250 ml of abs. diethyl ether, 270 ml of a 0.64N solution of n-butyllithium in abs. diethyl ether and 22.0 g of 1,3-dimethyl-4-piperidone: 1,3-dimethyl-4-(benzo[b]thien-2-yl)-4-piperidinol. The free base is recrystallised from hexane and melts at 118°–125°.

EXAMPLE 7

13.5 g (0.21 mole) of n-butyllithium in 145 ml of absolute diethyl ether is precooled to −70° to −80°. To this solution there is then added dropwise within 30 minutes, at a temperature of −70°, a solution of 42.6 g of 3-bromobenzo[b]thiophene in 250 ml of absolute diethyl ether. The solution is thereupon stirred for a further 30 minutes at −70°. An addition is then made dropwise, in the course of 30 minutes, of a solution of 23.5 g of 1-methyl-4-piperidone in 100 ml of absolute diethyl ether; the reaction temperature is held by external cooling at −70°, and the reaction solution is subsequently stirred for a further 10 hours at −70°. The reaction solution is thereupon heated to −5°, and 300 ml of water is added dropwise. The organic phase is separated, and the aqueous phase is extracted twice with 400 ml of ethyl acetate. The organic phases are combined, dried with sodium sulphate, filtered off with suction and concentrated by evaporation. The residue is dissolved in 500 ml of 2N hydrochloric acid, and the acid solution is washed with ether. The aqueous solution is then adjusted be addition by 10% sodium hydroxide solution to have a pH-value of 12, and extracted with one litre of chloroform. The chloroform solution is dried with sodium sulphate, filtered off with suction and concentrated by evaporation to obtain crude 1-methyl-4-(benzo[b]thien-3-yl)-4-piperidinol. The free base melts at 150°–151° after recrystallisation from acetone.

The hydrochloride is obtained with hydrogen chloride in ethyl acetate. On recrystallisation from aqueous acetone, it is obtained as monohydrate having a melting point of 135°–145°.

EXAMPLE 8

15.0 g of 1-methyl-4-(benzo[b]thien-3-yl)-4-piperidinol is refluxed for 6 hours in 150 ml of glacial acetic acid and 45 ml of 12N hydrochloric acid. The solution is cooled to room temperature; it is brought to the pH-value of 12 by the addition of 2N sodium hydroxide solution, and extracted three times with 250 ml of methylene chloride each time. The methylene chloride solutions are thereafter washed with 2N sodium hydroxide solution and finally with water; they are combined, dried with sodium sulphate, filtered, and concentrated by evaporation. The residue is fractionally distilled in high vacuum: the fraction distilling off at 160°–170° and 0.3 Torr is 1-methyl-4-(benzo[b]thien-3-yl)-1,2,3,6-tetrahydropyridine. The base melts at 51°–53° after recrystallisation from hexane. The hydrochloride obtained with a solution of hydrogen chloride in ethyl acetate melts at 220°–222° after recrystallisation from ethyl acetate.

EXAMPLE 9

10.0 g of 1-methyl-4-(benzo[b]thien-3-yl)-1,2,3,6-tetrahydro-pyridine is dissolved in 100 ml of methanol, and hydrogenated in the presence of 16 g of palladium charcoal (5% Pd) at a temperature of 30° to 35° under a pressure of 3 bars. (Parr apparatus). After 65 hours, hydrogenation is interrupted with attainment of 100% of the theoretical hydrogen absorption; the catalyst is filtered off and the filtrate is concentrated in vacuo. The residue is fractionally distilled in vacuo. The fraction distilling off at 130° to 135° and 0.2 Torr is 1-methyl-4-(benzo[b]thien-3-yl)-piperidine. The hydrochloride prepared with a solution of hydrogen chloride in ethyl acetate melts at 230°–233° after recrystallisation from ethyl acetate.

EXAMPLE 10

11 g of 1-methyl-4-(benzo[b]thien-3-yl)-piperidine is dissolved in 120 ml of toluene. At a reaction temperature of 50°, 20 g of chloroformic acid ethyl ester is slowly added dropwise under a strong flow of nitrogen. The solution is thereupon stirred for 20 hours at 50°; a further 10 g of chloroformic acid ethyl ester is added dropwise and stirring is continued for 2 hours at 50°. The excess chloroformic acid ethyl ester is subsequently distilled off under normal pressure, the solution is cooled to 70°, filtered under suction and the filter residue is afterwards washed with 500 ml of toluene. The combined filtrates are successively washed with 500 ml of water, 800 ml of a 10% solution of methanesulphonic acid in water, 500 ml of water, 500 ml of 2N sodium hydroxide solution and 500 ml of water; they are dried with sodium sulphate, filtered and concentrated by evaporation. The resulting 4-benzo[b]thien-3-yl)-1-piperidinecarboxylic acid ethyl ester is dissolved in 110 ml of ethylene gylcol. After the addition of 13 g of solid sodium hydroxide, the formed cloudy solution is heated, with vigorous stirring, for 15 hours at 160°. The reaction solution is thereupon cooled to 20°, and extracted three times with 500 ml of ethyl acetate each time. The organic phases are washed 5 times with 1 litre of water each time, dried with sodium sulphate, filtered, combined, and concentrated by evaporation. The residue is dissolved in 500 ml of 2N hydrochloric acid and the acid solution is extracted with toluene. The aqueous solution is thereupon adjusted to have a pH-value of 12 by addition of 10% sodium hydroxide solution, and is then extracted with one litre of chloroform. The chloroform solution is dried with sodium sulphate, filtered and concentrated by evaporation; there is obtained crude 4-(benzo[b]-thien-3-yl)-piperidine. The hydrochloride is prepared with hydrogen chloride in ethyl acetate and recrystalised from acetone, whereupon it melts above 270°.

EXAMPLE 11

4.4 g of 4-(benzo[b]thien-2-yl)-piperidine is dissolved in 80 ml of benzene. An addition is made at room temperature of 5.0 g of methyl vinyl ketone, and the reaction solution is stirred for 15 hours at room temperature. The reaction solution is thereupon filtered and the clear filtrate is concentrated in vacuo. According to chromatographical analysis, the oily residue is homogeneous 1-(3-oxobutyl)-4-(benzo[b]thien-2-yl)-piperidine [2-[4-(benzo[b]thien-2-yl)-ethyl]-methyl-ketone]. The hydrochloride is prepared with hydrogen chloride in ethyl acetate and, after recrystallisation from acetone, melts at 185°.

EXAMPLE 12

26.5 ml of a 2N solution of n-butyllithium in hexane is added dropwise within 30 minutes to a solution of 7.0 g of benzo[b]thiophene in 50 ml of abs. diethyl ether at a reaction temperature of 5° to 10°. The solution is then stirred for a further 1 hour at 0°. There is then added dropwise, in the course of 30 minutes, a solution of 5.9 g of 1-methyl-3-piperidone in 50 ml of abs. diethyl ether, with the reaction temperature being maintained at 0° by external cooling. The reaction solution is stirred for a further 15 hours at room temperature, and is then poured, with stirring, onto 100 g of ice; the aqueous phase is separated, and extracted 3 times with 100 ml of ethyl acetate each time. The combined organic extracts are dried with sodium sulphate, filtered under suction and concentrated by evaporation. The residue is dissolved in 250 ml of 2N hydrochloric acid, and the acid solution is washed with diethyl ether. The aqueous solution is subsequently brought to a pH-value of 12 by the addition of 10 sodium hydroxide solution, and extracted with 500 ml of chloroform. The chloroform solution is dried with sodium sulphate, filtered with suction and concentrated by evaporation to obtain crude 1-methyl-3-(benzo[b]thien-2-yl)-3-piperidinol; the oxalate thereof is prepared, for example, from 1.8 g of free base in ethyl actate and 0.7 g of oxalic acid in 10 ml of ethyl acetate, and it melts at 165°–168° after recrystallisation from ethyl acetate.

EXAMPLE 13

28.0 g of 1,3-dimethyl-4-(benzo[b]thien-2-yl)-4-piperindinol is refluxed in 250 ml of glacial acetic acid and 60 ml of hydrochloric acid for 15 hours. The solution is concentrated in vacuo (12 Torr) and the residue is taken up in 2N hydrochloric acid, whereupon 1,3-dimethyl 4-(benzo[b]thien-2-yl)-1,2,3,6-tetrahydropyridine hydrochloride immediately crystallises out and is filtered off with suction; it melts at 211°14 213° after recrystallisation from acetone.

EXAMPLE 14

17.5 g of 1,3-dimethyl-4-(benzo[b]thien-2-yl)-1,2,3,6-tetrahydropyridine is dissolved in 200 ml of methanol, and hydrogenated in the presence of 5.0 g of palladium-charcoal catalyst (5% Pd) at a temperature of 30°–35° under normal pressure. Hydrogenation is interrupted after 42 hours with the attainment of 100% of the theoretical absorption of hydrogen; the catalyst is filtered off and the filtrate is concentrated in vacuo. The residue is dissolved in 500 ml of 2N hydrochloric acid and the acid solution is extracted with toluene. The aqeuous solution is thereupon adjusted to a pH-value of 12 by the addition of 10% sodium hydroxide solution, and then extracted with 500 ml of chloroform. The chloroform solution is dried with sodium sulphate, filtered, and concentrated by evaporation. The crude 1,3-dimethyl-4-(benzo[b]thien-2-yl)-piperidine remaining behind is recrystallised from pentane and thereupon melts at 75°–76°.

The hydrochloride is prepared with hydrogen chloride in ethyl acetate, and recrystallised from acetone; it then has a melting point of 216°–218°.

EXAMPLE 15

The whole amount of the 3-methyl-4(benzo[b]thien-2-yl)-1-piperidinecarboxylic acid ethyl ester obtained as crude product according to the following section (a) is dissolved in 100 ml of ethylene glycol. There is then added 30 g of solid potassium hydroxide, and the resulting cloudy solution is heated, with vigorous stirring, for 15 hours at 160°. The reaction solution is subsequently cooled to 20°, and extracted 3 times with 150 ml of toluene each time. The combined toluene solutions are washed 5 times with 250 ml of water each time, and subsequently extracted twice with 200 ml of 2N hydrochloric acid each time. The acid solutions are combined; the pH-value is adjusted to 12 by the addition of 10% sodium hydroxide solution, and extraction is performed with 500 ml of chloroform. The chloroform solution is dried with sodium sulphate, filtered, and concentrated by evaporation to obtain crude 3-methyl-4-(benzo[b]thien-2-yl)-piperidine. The crude base is distilled in a bulb tube (molecular distillation) under high vacuum (0.20 Torr at a bath temperature of 170°–190°). From the distillate there is prepared the hydrochloride with hydrogen chloride in ethyl acetate; the hydrochloride is recrystallised from acetone and then melts at 253°–255°.

The 3-methyl-4-(benzo[b]thien-2-yl)-1-piperidinecarboxylic acid ehtyl ester used as starting material is produced as follows:

a. 9.5 g of 1,3-dimethyl-4-(benzo[b]thien-2-yl)-piperidine is dissolved in 200 ml of toluene. At a reaction temperature of 50°, there is slowly added dropwise, under a strong flow of nitrogen, 25 ml of chloroformic acid ethyl ester. The solution is thereupon stirred for 20 hours at 50°; a further 11 ml of chloroformic acid ethyl ester is added dropwise, and stirring is continued for 2 hours at 50°. The excess chloroformic acid ethyl ester is subsequently distilled off under normal pressure, the solution is cooled to 70°, filtered with suction, and the filter residue is afterwards washed with 250 ml of toluene. The combined filtrates are successively washed with 500 ml of water, 500 ml of a 10% solution of methanesulphonic acid in water, 500 ml of water 250 ml of 2N sodium hydroxide solution and 500 ml of water; they are dried with sodium sulphate, filtered, and concentrated by evaporation. The resulting crude 3-methyl-4-(benzo[b]thien-2-yl)-1-piperidinecarboxylic acid ethyl ester can be further used without additional purification.

EXAMPLE 16

Tablets containing 50 mg of active substance are produced in the following composition in the usual manner:

| Composition: | |
|---|---|
| 1-methyl-4-(benzo[b]thien-2-yl)-piperidine hydrochloride | 50 mg |
| wheat starch | 59 mg |
| lactose | 70 mg |
| colloidal silicic acid | 10 mg |
| talcum | 10 mg |
| magnesium stearate | 1 mg |
| | 200 mg |

PREPARATION PROCEDURE

1-Methyl-4-(benzo[b]thien-2-yl)-piperidine hydrochloride is mixed with a part of the wheat starch, with lactose and colloidal silicic acid, and the mixture is put through a sieve to obtain a pulverulent mixture. A further part of the wheat starch is mixed to a paste with the five-fold amount of water on a water-bath, and the powder mixture is kneaded with this paste until a slightly plastic mixture is obtained.

The plastic mixture is pressed through a sieve having a mesh size of about 3 mm; the sieved material is dried and the resulting dry granulate is again put through a sieve. The remaining wheat starch, talcum and magnesium stearate are then mixed in and the mixture is pressed to form grooved tablets each weighing 200 mg.

The daily dose is about ½ to 4 tablets in the case of a warm-blooded animal of about 75 kg body weight; however, the equivalent dose of active substance can be administered in a single correspondingly formulated tablet.

What I claim is:

1. A benzo[b]thiophene of the formula

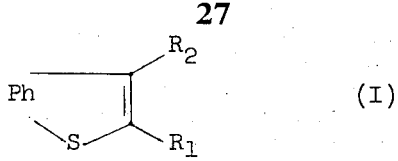

wherein Ph is o-phenylene unsubstituted or at most di-substituted by $C_1$–$C_4$-lower alkyl, $C_1$–$C_4$-lower alkoxy, chlorine or hydroxy, $R_1$ or $R_2$ is piperidyl which is saturated or contains a C–C-double bond emanating from the ring-C-atom bound to the benzo[b]thienyl radical, and, if saturated, at this C-atom is unsubstituted or substituted by hydroxy, and which at its other ring-C-atoms is unsubstituted or substituted by one methyl, and which at its N-atom is unsubstituted or substituted by $C_1$–$C_4$-lower alkyl, $C_3$–$C_4$-lower alkenyl, $C_3$–$C_4$-lower alkynyl, $C_3$–$C_6$-cycloalkyl-$C_1$–$C_4$-lower alkyl, benzyl, $C_1$–$C_4$-lower alkylbenzyl, $C_1$–$C_4$-lower alkoxybenzyl, halobenzyl, 2-phenethyl or α-methyl-2-phenethyl, and $R_2$ or $R_1$ is hydrogen or $C_1$–$C_4$-lower alkyl, and its pharmaceutically acceptable acid addition salts.

2. A compound according to claim 1 having the formula I given in claim 1, wherein Ph is o-phenylene unsubstituted or at most di-substituted by $C_1$–$C_4$-lower alkyl, $C_1$–$C_4$-lower alkoxy, chlorine or hydroxy, $R_1$ or $R_2$ is piperidyl which optionally contains a C–C-double bond emanating from the ring-C-atom bound to the benzo[b]thienyl radical, and which at its other ring-C-atoms is unsubstituted or substituted by one methyl, and which at its N-atom is unsubstituted or substituted by $C_1$–$C_4$-lower alkyl, $C_3$–$C_4$-lower alkenyl, $C_3$–$C_4$-lower alkynyl, $C_3$–$C_6$-cycloalkyl-$C_1$–$C_4$-lower alkyl, benzyl, $C_1$–$C_4$-lower alkyl benzyl, $C_1$–$C_4$-lower alkoxybenzyl, halobenzyl, 2-phenethyl or α-methyl-2-phenethyl, and $R_2$ or $R_1$ is hydrogen or $C_1$–$C_4$-lower alkyl, and its pharmaceutically acceptable acid addition salts.

3. A compound according to claim 1 having the formula I given in claim 1, wherein Ph is o-phenylene, $R_1$ or $R_2$ is piperidyl which optionally contains a C–C-double bond emanating from the ring-C-atom bound to the benzo[b]thienyl radical, and which at its other ring-C-atoms is unsubstituted or substituted by one methyl, and which at its N-atom is unsubstituted or substituted by $C_1$–$C_4$-lower alkyl, $C_3$–$C_4$-lower alkenyl, $C_3$–$C_4$-lower alkynyl, cyclopropylmethyl or benzyl, and $R_2$ or $R_1$ is hydrogen, and its pharmaceutically acceptable acid addition salts.

4. A compound according to claim 1 having the formula I given in claim 1, wherein Ph is o-phenylene, $R_1$ or $R_2$ is 4-piperidyl or 1,2,3,6-tetrahydro-4-pyridyl, which is unsubstituted or substituted in the 3-position by methyl, and which is unsubstituted or substituted at its N-atom by methyl, allyl, 2-propynyl or cyclopropylmethyl or benzyl, and $R_2$ or $R_1$ is hydrogen, and its pharmaceutically acceptable acid addition salts.

5. A compound according to claim 1 which is 1-methyl-4-(benzo[b]thien-2-yl)-1,2,3,6-tetrahydropyridine, and its pharmaceutically acceptable acid addition salts.

6. A compound according to claim 1 which is 1-methyl-4-(benzo[b]thien-2-yl)-piperidine, and its pharmaceutically acceptable acid addition salts.

7. A compound according to claim 1 which is 4-(benzo[b]thien-2-yl)-piperidine, and its pharmaceutically acceptable acid addition salts.

8. A compound according to claim 1 which is 1-(2-propinyl)-4-(benzo[b]thien-2-yl)-piperidine, and its pharmaceutically acceptable acid addition salts.

9. A compound according to claim 1 which is 1,3-dimethyl-4-(benzo[b]thien-2-yl)-4-piperidinol, and its pharmaceutically acceptable acid addition salts.

10. A compound according to claim 1 which is 1-methyl-4-(benzo[b]thien-3-yl)-1,2,3,6-tetrahydropyridine, and its pharmaceutically acceptable acid addition salts.

11. A compound according to claim 1 which is 1-methyl-4-benzo[b]thien-3-yl)-piperidine, and its pharmaceutically acceptable acid addition salts.

12. A compound according to claim 1 which is 4-(benzo[b]thien-3-yl)-piperidine, and its pharmaceutically acceptable acid addition salts.

13. A compound according to claim 1 which is 1,3-dimethyl-4-(benzo[b]thien-2-yl)-1,2,3,6-tetrahydropyridine.

14. A compound according to claim 1 which is 1,3-dimethyl-4-(benzo[b]thien-2-yl)-piperidine, and its pharmaceutically acceptable acid addition salts.

15. A compound according to claim 1 which is 3-methyl-4-(benzo[b]thien-2-yl)-piperidine, and its pharmaceutically acceptable acid addition salts.

16. A pharmaceutical preparation for the treatment of mental depression and psychoses comprising a therapeutically effective amount of a compound according to claim 1 which corresponds to the formula

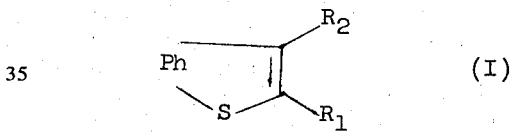

wherein Ph is o-phenylene unsubstituted or at most di-substituted by $C_1$–$C_4$-lower alkyl, $C_1$–$C_4$-lower alkoxy, chlorine or hydroxy, $R_1$ or $R_2$ is piperidyl which is saturated or contains a C–C-double bond emanating from the ring-C-atom bound to the benzo[b]thienyl radical, and, if saturated, at this C-atom is unsubstituted or substituted by hydroxy and which at its other ring-C-atoms is unsubstituted or substituted by one methyl, and which at its N-atom is unsubstituted or substituted by $C_1$–$C_4$-lower alkyl, $C_3$–$C_4$-lower alkenyl, $C_3$–$C_4$-lower alkynyl, $C_3$–$C_6$-cycloalkyl-$C_1$–$C_4$-lower alkyl, benzyl, $C_1$–$C_4$-lower alkylbenzyl, $C_1$–$C_4$-lower alkoxybenzyl, halobenzyl, 2-phenethyl or α-methyl-2-phenethyl, and $R_2$ or $R_1$ is hydrogen or $C_1$–$C_4$-lower alkyl, or of a pharmaceutically acceptable acid addition salt thereof together with a pharmaceutical carrier material.

17. A pharmaceutical preparation for the treatment of mental depression and psychoses according to claim 16, in which a therapeutically effective amount of a compound of formula I given in claim 16, wherein Ph is o-phenylene unsubstituted or at most di-substituted by $C_1$–$C_4$-lower alkyl, $C_1$–$C_4$-lower alkoxy, chlorine or hydroxy, $R_1$ or $R_2$ is piperidyl which is saturated or contains a C–C-double bond emanating from the ring-C-atom bound to the benzy[b]thienyl radical, and which at its other ring-C-atoms is unsubstituted or substituted by one methyl, and which at its N-atom is unsubstituted or substituted by C₁–C₄-lower alkyl, C₃–C₄-lower alkenyl, C₃–C₄-lower alkynyl, C₃–C₆-cycloalkyl-C₁–C₄-lower alkyl, benzyl, C₁–C₄-lower alkylbenzyl, C₁–C₄-lower alkoxybenzyl, halobenzyl, 2-phenethyl or α-methyl-2-phenethyl, and R₂ or R₁ is hydrogen or C₁–C₄-lower alkyl, or of a pharmaceutically acceptable acid addition salt thereof together with a pharmaceutical carrier material.

18. A pharmaceutical preparation for the treatment of mental depression and psychoses according to claim 16, in which a therapeutically effective amount of a compound of formula I given in claim 16, wherein Ph is o-phenylene, R₁ or R₂ is piperidyl which is saturated or contains a C–C-double bond emanating from the ring-C-atom bound to the benzy[b]thienyl radical, and which at its other ring-C-atom is unsubstituted or substituted by one methyl, and which at its N-atom is unsubstituted or substituted by C₁–C₄-lower alkyl, C₃–C₄-lower alkenyl, C₃–C₄-lower alkynyl, cyclopropylmethyl or benzyl, and R₂ or R₁ is hydrogen, or of a pharmaceutically acceptable acid addition salt thereof together with a pharmaceutical carrier material.

19. A pharmaceutical preparation for the treatment of mental depression and psychoses according to claim 16, in which a therapeutically effective amount of a compound of formula I given in claim 16, wherein Ph is o-phenylene, R₁ or R₂ is 4-piperidyl or 1,2,3,6-tetrahydro-4-pyridyl, which is unsubstituted or substituted in the 3-position by methyl, and which is unsubstituted or substituted at its N-atom by methyl, allyl, 2-propynyl or cyclopropylmethyl or benzyl, and R₂ or R₁ is hydrogen, or of a pharmaceutically acceptable acid addition salt thereof together with a pharmaceutical carrier material.

20. A method for the treatment of mental depression in a warm-blooded animal comprising administration to said animal of a therapeutically effective amount of a compound according to claim 1, which corresponds to the formula I,

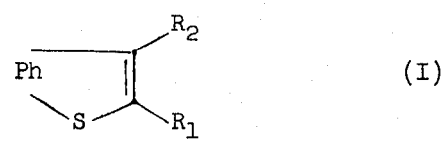

wherein Ph is o-phenylene unsubstituted or at most di-substituted by C₁–C₄-lower alkyl, C₁–C₄-lower alkoxy, chlorine or hydroxy, R₁ or R₂ is piperidyl which is saturated or contains a C–C-double bond emanating from the ring-C-atom bound to the benzo[b]thienyl radical, and, if saturated, at this C-atom is unsubstituted or substituted by hydroxy, and which at its other ring-C-atoms is unsubstituted or substituted by one methyl, and which at its N-atom is unsubstituted or substituted by C₁–C₄-lower alkyl, C₃–C₄-lower alkenyl, C₃–C₄-lower alkynyl, C₃–C₆-cycloalkyl-C₁–C₄-lower alkyl, benzyl, C₁–C₄-lower alkylbenzyl, C₁–C₄-lower alkoxybenzyl, halobenzyl, 2-phenethyl or α-methyl-2-phenethyl, and R₂ or R₁ is hydrogen or C₁–C₄-lower alkyl, or of a pharmaceutically acceptable acid addition salt thereof.

21. A method according to claim 20, wherein a compound of the formula I given in claim 20, in which Ph is o-phenylene unsubstituted or at most di-substituted by C₁–C₄-lower alkyl, C₁–C₄-lower alkoxy, chlorine or hydroxy, R₁ or R₂ is piperidyl which is saturated or contains a C–C-double bond emanating from the ring-C-atom bound to the benzo[b]thienyl radical, and which at its other ring-C-atoms is unsubstituted or substituted by one methyl, and which at its N-atom is unsubstituted or substituted by C₁–C₄-lower alkyl, C₃–C₄-lower alkenyl, C₃–C₄-lower alkynyl, C₃–C₆-cycloalkyl-C₁–C₄-lower alkyl, benzyl, C₁–C₄-lower alkylbenzyl, C₁–C₄-lower alkoxybenzyl, halobenzyl, 2-phenethyl or α-methyl-2-phenethyl, and R₂ or R₁ is hydrogen or C₁–C₄-lower alkyl, or a pharmaceutically acceptable acid addition salt thereof is used.

* * * * *